United States Patent
Marmaropoulos et al.

(10) Patent No.: US 7,211,053 B2
(45) Date of Patent: *May 1, 2007

(54) SELECTIVELY APPLIED WEARABLE MEDICAL SENSORS

(75) Inventors: George Marmaropoulos, Thessaloniki (GR); Clive van Heerden, London (GB)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/842,380

(22) Filed: May 10, 2004

(65) Prior Publication Data

US 2004/0210165 A1    Oct. 21, 2004

Related U.S. Application Data

(63) Continuation of application No. 10/043,380, filed on Oct. 26, 2001, now Pat. No. 6,755,795.

(51) Int. Cl.
*A61B 5/117* (2006.01)
*A61B 5/103* (2006.01)

(52) U.S. Cl. .................................... 600/587
(58) Field of Classification Search ............... 600/300, 600/301, 386–390, 481, 509, 529, 534, 544, 600/546, 547, 549; 73/379.01; 2/1, 69; 128/897, 898
See application file for complete search history.

(56) References Cited

U.S. PATENT DOCUMENTS

| 5,454,376 | A | * | 10/1995 | Stephens et al. ............. 600/534 |
| 5,683,404 | A | * | 11/1997 | Johnson ...................... 606/151 |
| 5,802,611 | A | * | 9/1998 | McKenzie et al. ................ 2/69 |
| 6,198,394 | B1 | * | 3/2001 | Jacobsen et al. ......... 340/573.1 |
| 6,346,025 | B1 | * | 2/2002 | Tachau et al. ................. 446/71 |
| 6,487,906 | B1 | * | 12/2002 | Hock ....................... 73/379.01 |
| 6,551,252 | B2 | * | 4/2003 | Sackner et al. ............. 600/536 |
| 6,755,795 | B2 | * | 6/2004 | Marmaropoulos et al. .. 600/587 |
| 2002/0032386 | A1 | * | 3/2002 | Sackner et al. ............. 600/536 |

* cited by examiner

*Primary Examiner*—Max F. Hindenburg
*Assistant Examiner*—Brian Szmal

(57) ABSTRACT

A wearable garment includes sensor device of well-know design that are selectively pressed against the skin of the wearer when it is desired to obtain sensor readings, such as heart rate or temperature, or to apply treatment such as electrical pulses for defibrillation purposes. The garment incorporates one or more bands of flexible material that circumscribe portions of the wearer's body, with at least one sensor device positioned on the garment between the band and the wearer's body. To assure the comfort of the wearer, the circumference of the band can be shortened selectively from a first dimension, which loosely circumscribes a desired portion of the wearer's body, to a second, lesser dimension, which more tightly circumscribes the wearer's body and presses the sensor-securely into contact with the wearer's skin.

13 Claims, 2 Drawing Sheets

SELECTIVELY APPLIED WEARABLE MEDICAL SENSORS

This is a Continuation of application Ser. No. 10/043,380, filed Oct. 26, 2001 and issued as U.S. Pat. No. 6,755,795.

BACKGROUND OF THE INVENTION

1. Field of the Invention

This invention relates to sensors used in the electrical treatment and monitoring of human and animal bodies. More specifically, the invention relates to wearable garments that allow sensor devices to be pressed selectively against the skin of the wearer when it is desired to obtain medical information or to apply treatment by contact with the surface of the skin.

2. Description of the Invention

Sensing and treatment devices for contacting the surface of the skin are well-known in the art. It is also well-known that such devices require tight-fitting, e.g. elevated unit pressure, contact with the skin. However, the incorporation of such sensors into wearable garments that provide for applying sensors to the skin of a wearer with selective and/or variable pressure, is not well-known.

In the prior art, sensors are either adhered directly to the skin of the wearer using well-known types of adhesive materials or, they are tightly strapped to the user's body using suitable straps or bands having buckles or other clasping mechanisms adapted to the purpose. Such prior art apparatus for affixing sensors to the skin of a user do not take the user's comfort into consideration by allowing the pressure of the sensor against the skin to be increased easily only when the sensor is in use.

The present invention overcomes these problems and limitations of the prior art by allowing sensors to be pressed against the skin of a wearer selectively, only when needed or desired. The sensors are mounted on the inside of a wearable garment, and the garment incorporates circumscribing bands that can be reduced in diameter, selectively, to press the sensors against the skin of one wearing the garment.

SUMMARY OF THE INVENTION

The present invention discloses a wearable garment that incorporates one or more skin-contacting sensor devices positioned to contact the skin surface of a user wearing the garment. The wearable garment of this invention incorporates one or more bands of flexible material that circumscribe portions of the wearer's body with at least one sensor device positioned between the band and the wearer. The circumference of the band can be shortened from a first dimension, which loosely circumscribes the desired portion of the wearer's body, to a second, lesser dimension, which securely presses the sensor into contact with the wearer's skin.

In accordance with this invention, the band may be tightened about the wearer's body either by drawing the ends of a loop about the body in the nature of a drawstring or by shrinking the overall length of the material of a continuous loop as by passing an electrical current through a continuous loop made of shape Memory Alloy Wire. In this regard, the band may be loosely incorporated into the body of the garment in the well-known manner of a drawstring or, the band may be integrated into the body of the garment as by forming a desired portion of the fabric material from different fibers such as fibers comprising Shape Memory alloy. To utilize the electrically responsive shrinkage characteristics of shape-memory alloy material in a convenient manner, the garment may be provided with means for supporting or otherwise carrying with it, a portable electrical power supply such as a battery.

Further in accordance with this invention, it may be noted that any treatment or monitoring equipment that relies upon the sensors carried by the wearable garment, may incorporate internal features such as a programmable microprocessor to activate a band formed of shape memory alloy, at a predetermined rate or in accordance with a predetermined schedule.

These and other and further features and advantages of this invention will be made more apparent to those having skill in this art, by reference to the following specification considered in conjunction with the accompanying drawings, in which:

DETAILED DESCRIPTION OF THE DISCLOSED EMBODIMENT

In the following description, for purposes of explanation rather than limitation, specific details are set forth such as the particular architecture, interfaces, techniques, etc., in order to provide a thorough understanding of the present invention. For purposes of simplicity and clarity, detailed descriptions of well-known devices, circuits, and methods are omitted so as not to obscure the description of the present invention with unnecessary detail.

Figure 1:
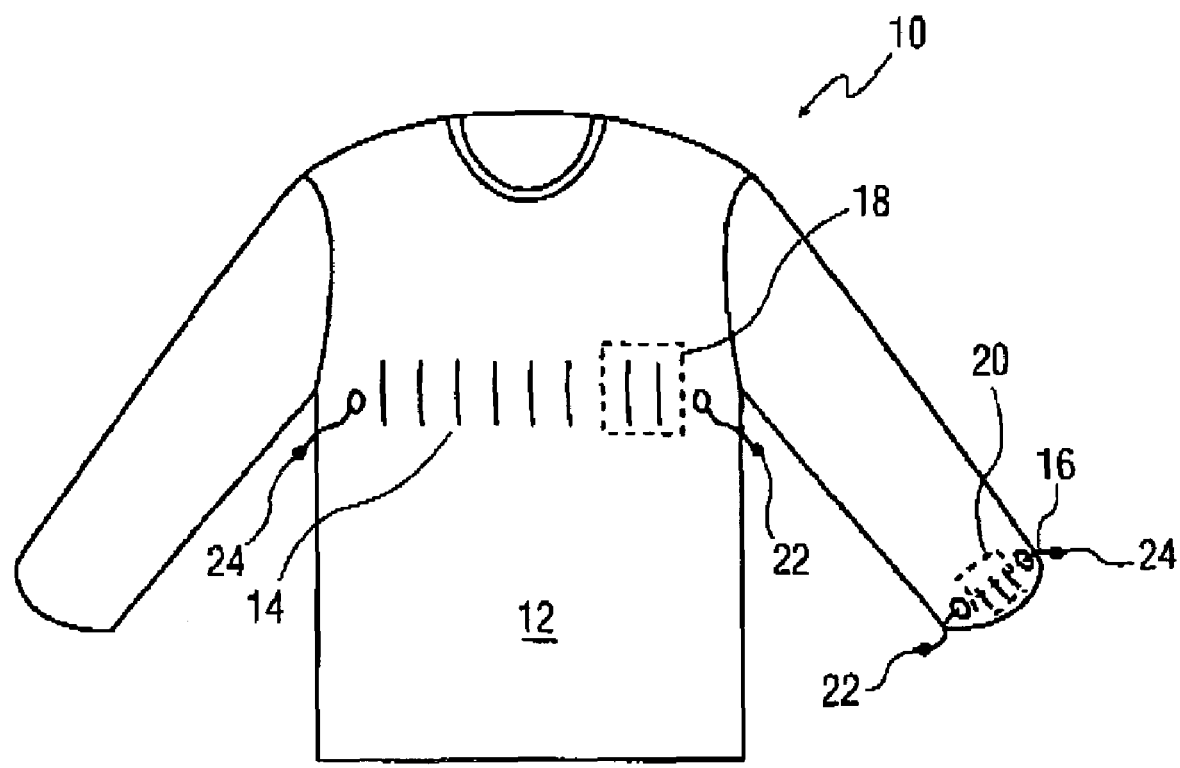
FIG. 1 is a front plan view of a wearable garment in accordance with this invention, incorporating two separate drawstrings positioned to apply two separate sensors to the skin of a wearer.

Referring now to FIG. 1 of the drawings, a wearable shirt garment 10 in accordance with this invention may be seen to comprise a wearable body structure 12 having a first constriction band 14 coupled to the body 12 in the form of a drawstring circumscribing the chest area of a wearer, and a second constricting drawstring 16 circumscribing a wrist area. Shown in dotted lines representing a position on the interior (invisible) surface of garment 10, a first sensor device 18 is positioned so that it will lie between the band 14 and the chest skin of one wearing the garment 10. A second sensor 20 is similarly positioned to lie between band 16 and the wrist skin of a wearer.

It should be understood readily by those having skill in this art, that the number and positioning of the bands 14, 16 and the sensors 18, 20 is illustrative only, and other or different sensors, or different number of sensors, in other or different locations may be incorporated into this or any differently shaped garment without departing from the spirit and scope of this invention. For example, in the absence of any desire for a sensor in a wrist area, the garment may be made essentially sleeveless in form, if desired. Similarly, the garment may assume other forms, such as, for example, trousers rather than a shirt or vest, or even, perhaps, a simple wrist or arm band.

Bands 14, 16 define loops positioned so as to substantially circumscribe desired portions of the anatomy of the wearer of the garment 10 in a loose-fitting loop, and they are configured to have a first circumferential loop dimension that circumscribes the wearer's body in a loose, non-confining fit. In the embodiment illustrated in FIG. 1, bands 14, 16 are coupled to the body structure 12 in the manner of a drawstring that is looped around the anatomy of a wearer when the body structure is being worn. Further, the bands are provided with free ends 22, 24, that can be drawn in opposite directions to reduce the circumferential dimension of the loop from a first value to a second value that is less than the first. When the circumferential dimension of the loop is reduced in this way, the corresponding band constricts the body of the wearer of garment 10, and presses the corresponding sensor device 18, 20 against the wearer's skin.

Figure 2:
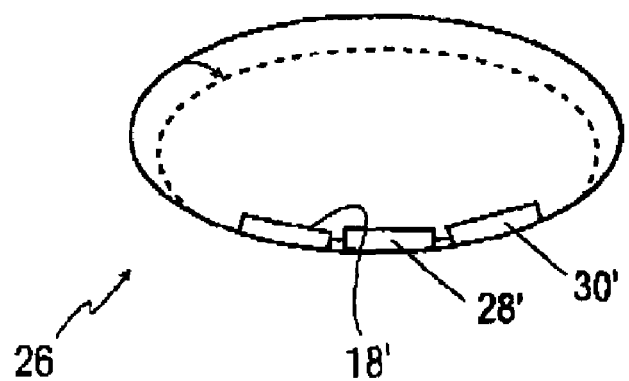
FIG. 2 is a pictorial representation of an alternative embodiment of an electrically activatable band usable in accordance with this invention in lieu of the drawstring of FIG. 1; and, FIG. 3 is a front plan view of an alternative embodiment of a wearable garment in accordance with this invention, incorporating constriction bands formed of a shape-memory material that is constrictable in response to the flow of electricity therethrough.

As mentioned earlier herein, FIG. 2 illustrates an alternative form of constriction band 26, having the form of a continuous, or closed, loop formed of shape memory alloy fibers having a first loose-fitting circumferential dimension. In the well-known manner of shape memory alloy materials, the first circumferential dimension of loop 26 may be reduced to a lesser second dimension so as to constrict an interposed sensor device 18' into contact with a wearer's body in accordance with this invention, by passing an electrical current, from a battery 28' for example, through the material of the loop. If desired, this embodiment of the invention may incorporate a suitable microprocessor 30' coupled with a source of electrical power such as battery 28', to control the application of electrical current to the band. In this manner, constriction of the band 26 may be made to take place periodically or in association with any desired external activity, such as the activation of an apparatus associated with use of sensors such as sensor 18', shown in FIG. 3.

Figure 3:
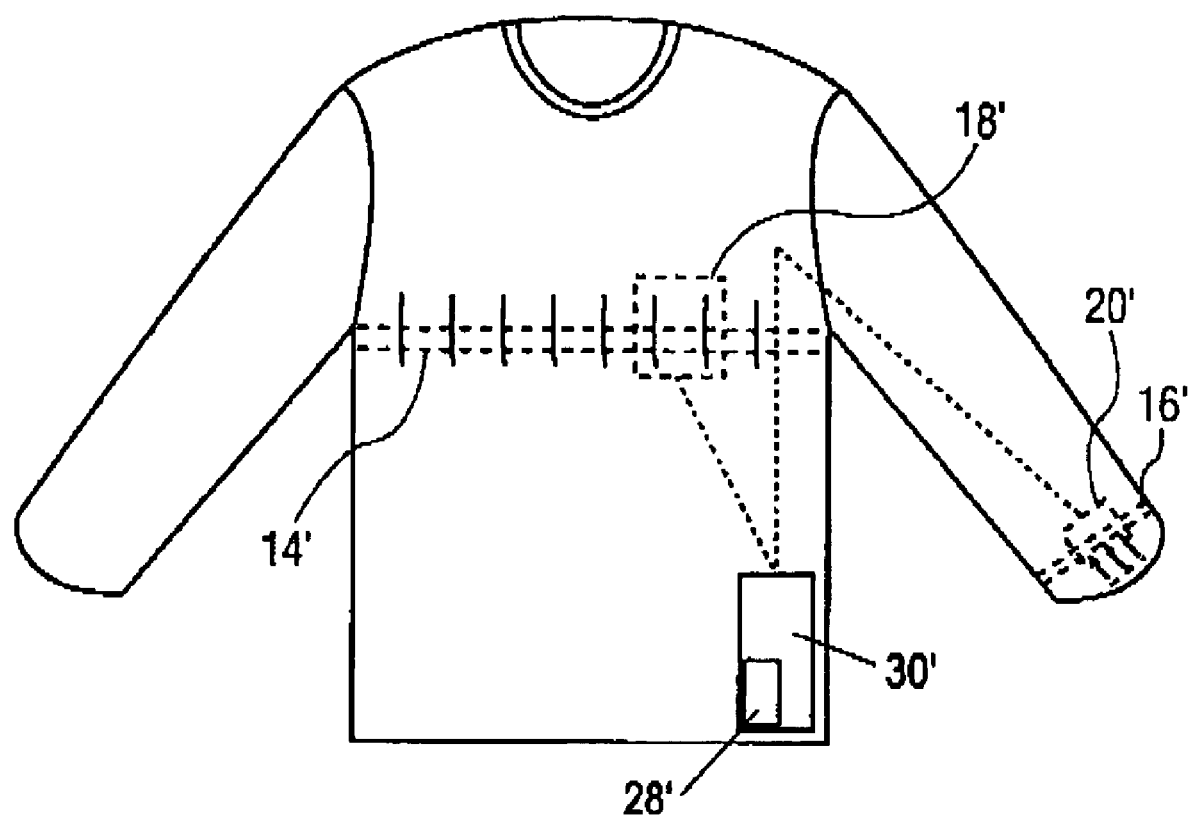

Referring to FIG. 3, bands 14', 16' can be integrated with the fabric of a wearable structure using conventional methods and can be of any natural or man made material sufficient to accomplish operations consistent with the requirements of the embodiments of the present disclosure, including, for example, Nitinol. Bands 14', 16' can also have different arrangements suitable to operatively interact with different sensors 18', 20' associated with the wearable structure in different ways, and so as to accommodate different applications.

The fabric of the garment body structure 12 may be any suitable material usable for garments, consistent with the requirements of the embodiments of the invention described herein. Similarly, the material of the bands 14, 16 may be any suitable flexible material consistent with this disclosure.

While the preferred embodiments of the present invention have been illustrated and described, it will be understood by those skilled in the art that various changes and modifications may be made, and equivalents may be substituted for elements thereof without departing from the true scope of the present invention. In addition, many modifications may be made to adapt to a particular situation and the teaching of the present invention without departing from the central scope. Therefore, it is intended that the present invention not be limited to the particular embodiment disclosed as the best mode contemplated for carrying out the present invention, but that the present invention include all embodiments falling within the scope of the appended claims.

Referring to FIG. 3, bands 14', 16' can be integrated with the fabric of a wearable structure using any of a variety of conventional methods for weaving, sewing or knitting and can be of any natural or man made material sufficient to accomplish operations consistent with the requirements of the embodiments of the present disclosure, including, for example, Nitinol. Bands 14', 16' can also have different configurations suitable to operatively interact with different sensors 18', 20' associated with the wearable structure so as to accommodate different applications.

The invention claimed is:

1. A garment for applying at least one sensor against the skin of a wearer, said garment comprising:
   a sensor mounted to said garment in position to contact a desired portion of the anatomy of a wearer of said garment;
   a band of flexible material incorporated into said garment in position to circumscribe a desired portion of the wearer's anatomy with said sensor being positioned to lie between said band and the wearer's anatomy;
   said band of flexible material defining a loop having a first circumferential dimension, and including both manual and automatic adjusting means for selectively reducing, at a predetermined or variable pressure rate, said first circumferential dimension to a second circumferential dimension less than said first circumferential dimension so as to constrict the anatomy of a wearer of said garment and press said sensor against said anatomy.

2. The garment of claim 1, wherein said flexible material of said band is axially elastic.

3. The garment of claim 1, wherein said adjusting means includes a shape memory alloy that reduces in axial length in response to the passage of electrical current therethrough.

4. The garment of claim 1, wherein said garment has the shape of a shirt.

5. The garment of claim 1, wherein said sensor is positioned to contact the chest of a wearer.

6. The garment of claim 1, wherein said adjusting means includes one or more drawstrings.

7. A method of selectively applying at least one sensor against the anatomy of a subject, said method comprising the steps of:
   positioning said sensor adjacent a desired portion of the anatomy of said subject;
   surrounding said sensor and said subject with a constrictable band of flexible material incorporated into a wearable structure; and
   constricting said constrictable band in association with an external activity at a predetermined or variable pressure rate to press said sensor into contact with the anatomy of said subject by adjusting means forming a component of said constrictable band and being capable of both manual and automatic operation.

8. The method of claim 7, wherein said adjusting means includes a shape memory alloy that reduces in axial length in response to the passage of electrical current therethrough.

9. The method of claim 7, wherein said adjusting means includes one or more drawstrings.

10. The garment of claim 3, wherein said shape memory alloy is Nitinol.

11. The garment of claim 3, further comprising a microprocessor suitable to activate said shape memory alloy according to a predetermined schedule.

12. A garment for applying a sensor to the skin of a wearer, said garment comprising:
   a sensor operatively associated with said garment so as to contact a desired portion of the wearer's anatomy;
   a flexible band incorporated into said garment in position to circumscribe a desired portion of the wearer's anatomy with said sensor being positioned to lie between said flexible band and the wearer's anatomy, wherein said flexible band is adjustable between at least two dimensions, a first dimension and a second dimension that differs from said first dimension, and includes both manual and automatic adjusting means for periodically, at a predetermined or variable pressure rate, adjusting the dimension thereof.

13. The garment of claim 12, further comprising a shape memory alloy that reduces in axial length in response to the passage of electrical current therethrough, and a microprocessor suitable to activate said shape memory alloy according to said predetermined or variable pressure rate.

* * * * *